United States Patent
Wan et al.

(10) Patent No.: US 9,891,204 B2
(45) Date of Patent: Feb. 13, 2018

(54) HEAVY METAL DETECTING DEVICE AND THE FABRICATING METHOD THEREOF

(71) Applicant: National Tsing Hua University, Hsinchu (TW)

(72) Inventors: De-Hui Wan, Hsinchu (TW); Shih-Yu Tseng, Hsinchu (TW); Shang-Yi Yi, Hsinchu (TW)

(73) Assignee: National Tsing Hua University, Hsinchu (TW)

(*) Notice: Subject to any disclaimer, the term of this patent is extended or adjusted under 35 U.S.C. 154(b) by 0 days.

(21) Appl. No.: 15/483,441

(22) Filed: Apr. 10, 2017

(65) Prior Publication Data
US 2017/0212092 A1    Jul. 27, 2017

Related U.S. Application Data

(62) Division of application No. 15/130,689, filed on Apr. 15, 2016.

(30) Foreign Application Priority Data

Aug. 10, 2015   (TW) .................................. 104125978

(51) Int. Cl.
G01N 33/18    (2006.01)
G01N 33/20    (2006.01)
(Continued)

(52) U.S. Cl.
CPC ........... *G01N 33/1813* (2013.01); *B08B 3/04* (2013.01); *G01N 21/554* (2013.01); *G01N 21/78* (2013.01);
(Continued)

(58) Field of Classification Search
CPC .. G01N 21/554; G01N 21/78; G01N 33/1813; G01N 33/20; G01N 1/28;
(Continued)

(56) References Cited

U.S. PATENT DOCUMENTS

| 6,515,749 B2* | 2/2003 | Pipino .................. G01N 21/554 356/440 |
| 2003/0124528 A1* | 7/2003 | Mirkin ..................... B82Y 5/00 435/6.12 |

(Continued)

FOREIGN PATENT DOCUMENTS

| CN | 102269706 A | 12/2011 |
| CN | 104471378 A | 3/2015 |

*Primary Examiner* — Maureen Wallenhorst
(74) *Attorney, Agent, or Firm* — Patterson+Sheridan, LLP (57) ABSTRACT

The present invention provides a heavy metal detecting device and the fabricating method thereof. The heavy metal detecting device includes a substrate and a nano-metal-particle array. The fabricating method of the heavy metal detecting device includes following steps of: (S1) preparing a substrate, cleaning the substrate with a first liquid, and drying the substrate with a first gas; (S2) soaking the substrate in a first solution; (S3) after soaking the substrate for a first period of time, cleaning and drying the substrate with the first liquid and the first gas respectively; (S4) soaking the substrate in a pre-synthesized nano-metal-particle solution; and (S5) after soaking the substrate for a second period of time, cleaning and drying the substrate with a second liquid and the first gas respectively. Compared to the prior arts, the heavy metal detecting device of the present invention has the advantages of simplicity and rapidity.

4 Claims, 9 Drawing Sheets

(51) Int. Cl.
    *B08B 3/04*         (2006.01)
    *G01N 21/552*     (2014.01)
    *G01N 21/78*      (2006.01)
    *G01N 21/77*      (2006.01)
    *G01N 1/28*       (2006.01)
    *G01N 1/34*       (2006.01)

(52) U.S. Cl.
    CPC ........... *G01N 33/20* (2013.01); *G01N 1/2813* (2013.01); *G01N 1/34* (2013.01); *G01N 2021/7773* (2013.01)

(58) Field of Classification Search
    CPC .................. G01N 1/2813; G01N 1/34; G01N 2021/7773; Y10T 436/25; Y10T 436/25125; B08B 3/04
    USPC ................. 436/73, 80, 81, 83, 84, 174, 175; 134/26, 30
    See application file for complete search history.

(56) References Cited

U.S. PATENT DOCUMENTS

| | | | |
|---|---|---|---|
| 2010/0265500 A1 | 10/2010 | Xia et al. | |
| 2015/0177138 A1* | 6/2015 | Kim ................. | G01N 33/54346 435/288.7 |

\* cited by examiner

HEAVY METAL DETECTING DEVICE AND THE FABRICATING METHOD THEREOF

CROSS-REFERENCE TO RELATED APPLICATION

This application is a divisional application of U.S. Ser. No. 15/130,689 filed Apr. 15, 2016, which claims priority from TW Patent Application No. 104125978, filed Aug. 10, 2015, both of which are incorporated herein by reference in their entireties.

BACKGROUND OF THE INVENTION

1. Field of the Invention

The present invention relates to a heavy metal detecting device and the fabricating method thereof, and more particularly, the present invention relates to a heavy metal detecting device and the fabricating method thereof with on-site quick detecting characteristic.

2. Description of the Prior Art

According to the announcement of EPA of Taiwan, the standard detecting method for detecting the Hg ions in the ground water is known as "the metal in the water and the micro-element detecting method, inductively coupled plasma atomic emission spectroscopy (W311.53C). This method can improve the accuracy of the analysis of the micro-element for detecting the different metal ions in the sample and further reach the limit of detecting the Hg ions up to $2\times10^{-5}$ mg/L, which is extremely suitable for detecting the heavy metal pollution. However, expensive devices, experienced operators and complicate process are required for this method, so the government needs to spend lots of time and money to monitor the environmental pollution. If the analysis is able to be done quickly on the spot and only the samples with the positive test brought back to the laboratory, the cost will be down because the amount of the samples is greatly decreased. That is to say, it will save money and time for monitoring. Nowadays, the heavy metal pollution is usually on-site detected by X-Ray Fluorescence (XRF). XRF is a device which emits X-ray with high power to light the analyte, and the user conducts the qualitative and quantitative analysis on the intensity of the power of the light. XRF has many advantages like rapidity, convenience and non-destruction. However, XRF has many disadvantages such as expensive (for example, one million Taiwan dollars per device), easy to be affected by the spectrum of the different elements (for example, the spectrum of Pb and Hg is duplicable), easy to be affected by the environmental factors like the temperature and the liquid sample, and insensitive to some elements (for example, the detection limit for Hg ranges from 20 mg/L to 50 mg/L). Therefore, the detecting technique for detecting the Hg pollution has a large room for improvement. Namely, there are a lot of business opportunities.

On the other side, because the nano-metal-particle has specific physical and chemical property, the nano-metal-particle is applied on the chemical detecting devices and photoelectric application. For example, the nano-metal-particle has a specific optical phenomenon—surface plasmon resonance (SPR). The resonance generated by the electromagnetic wave interacting with the electron of the metal when the electromagnetic wave with specific wavelength lights to the nano-metal-particle is called SPR. More importantly, SPR is affected by the composition, shape and size of the particle and the environment surrounding the particle. Besides, the nano-metal particle has high ratio of the surface area and adequate chemical characteristic on its surface, which can be easily changed by modifying the ligand/surfactant molecules being adsorbed on its surface. The function is able to be different by modifying the functional group, which makes it be widely used in a variety of chemical and biological analysis technology. For example, Au nano-particle with positive or negative surface has high dissolving characteristic in the solution, and the Au nano-particle will appear red when the peak of the absorption is 520 nm. When the surface of Au nano-particle reacts with the specific analytes, the particles get together because the surface-charge is neutralized, or there is a connection between two nano-particles. When the particles get together, the distance between the two particles is changed, and then the state of SPR is changed. At this moment, the absorption peak red-shifts between 600 nm to 700 nm, the color of the solution becomes blue. When the concentration of the analyte changes, the color changes as well. The change of the color is able to be observed by eyes or be analyzed by the spectrometer. Thus, the chemical detecting device is invested by utilizing the colorimetric method.

In recent years, Au nano-particle is widely used as the probe of the colorimetric method worldwide. The detecting targets comprise heavy metal ion, glucose, protein and DNA. A lot of people pay high attention on this method. Professor Mirkin and his research team published that the Au nano-particle modified with DNA can be used as colorimetric probe for detecting Hg ions by utilizing the thymine-$Hg^{2+}$-thymine to form the connection among the Au nano-particles, which made the particles get together and the color changed, and the limit of detecting was reached to 0.01 mg/L. Professor Xiaodong Chen and his research team simplified the complication of the synthesis. They used the uric acid to be the surface decoration of the Au nano-particle and achieved the detecting limit, $[Hg^{2+}]=0.01$ mg/L. However, even though the Hg detecting method with utilizing Au nano-particles can achieve very low detecting concentration, it is complicate for the laboratories to do the process. The efficiency of the method is low. The solution used in the method is hard to carry, easy to leak and hard to reserve. Moreover, there are a lot of unavoidable human errors. When the detecting process is operated, the change of the color is not obvious. In the recent research, Professor Chien-Fu Chen made Au nano-particles react with Hg ions in the solution first, and dropped it on the filter paper to recognize the color until achieving the detecting concentration, to 0.01 mg/L. In this experiment, Au nano-particles solution is still needed to be the probe even though it has the problems mentioned above (hard to reserve, carry and process). So, there are a lot of rooms needed to be improved if it serves as a rapid detecting platform.

SUMMARY OF THE INVENTION

To solve the problems mentioned above, the inventor provides a heavy metal detecting device and the fabricating method with single-layer nano-metal-particle array on the surface of the substrate for detecting the concentration of the heavy metal ion in aqueous solution. The detecting process is simple and quick. The present invention is able to utilize the picture function like the smart phone to analyze the color of the sample polluted by the heavy metal ion.

A scope of the present invention is providing a heavy metal detecting device comprising a substrate, and a nano-metal-particle array. The nano-metal-particle array comprises a nano-metal-particle disposed on the substrate; wherein when the analyte contacts with the heavy metal detecting device, the heavy mental ion of the analyte reacts with the nano-metal-particle, and then the user is able to observe the color-change on the surface of the heavy metal detecting device to detect the concentration of the heavy metal ion.

The substrate is a nonconductive or a conductive substrate, and the nonconductive substrate is not limited to be made of glass.

Another scope of the present invention is providing a fabricating method of the heavy metal detecting device, comprising the following step of: (S1) preparing a substrate, cleaning the substrate with a first liquid, and drying the substrate with a first gas; (S2) soaking the substrate in a first solution; (S3) after soaking the substrate for a first period of time, cleaning and drying the substrate with the first liquid and the first gas respectively; (S4) soaking the substrate in a pre-synthesized nano-metal-particle solution; and (S5) after soaking the substrate for a second period of time, cleaning and drying the substrate with a second liquid and the first gas respectively. Wherein, the process of the heavy metal detecting device is done after finishing all of the steps mentioned above.

Comparing with the familiar art, the present invention provides a heavy metal detecting device with the advantages of simplicity and rapidity in the detecting method. The heavy metal detecting device is light, equipped with high sensitivity for detecting the concentration of the heavy metal ion in the analyte. The present invention provides a heavy metal detecting device to form a layer of the nano-metal-particle on the surface of the nonconductive substrate to process the fabricating of the heavy metal detecting device. The heavy metal detecting device is a portable and rapid detection platform with low-cost, stability and high sensitivity.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein:

FIG. 4(a)-4(h) shows the images from the scanning electron microscope of the present invention in an embodiment.

FIG. 5(a)-5(f) shows the spectrum diagram of the reflectance spectra of the heavy metal detecting device before and after reacting with the heavy metal ions with the different concentration.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1:
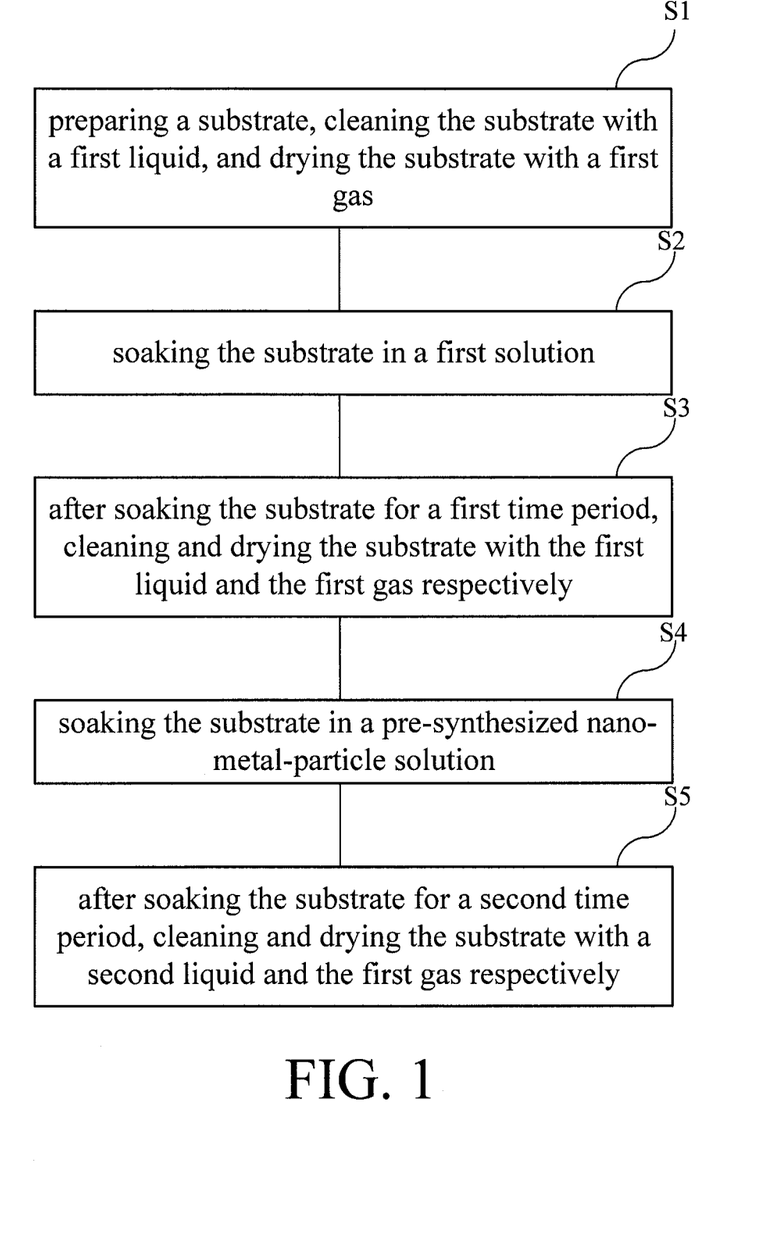
FIG. 1 shows the process flow chart of the heavy metal detecting device of the present invention in an embodiment.
Figure 2:
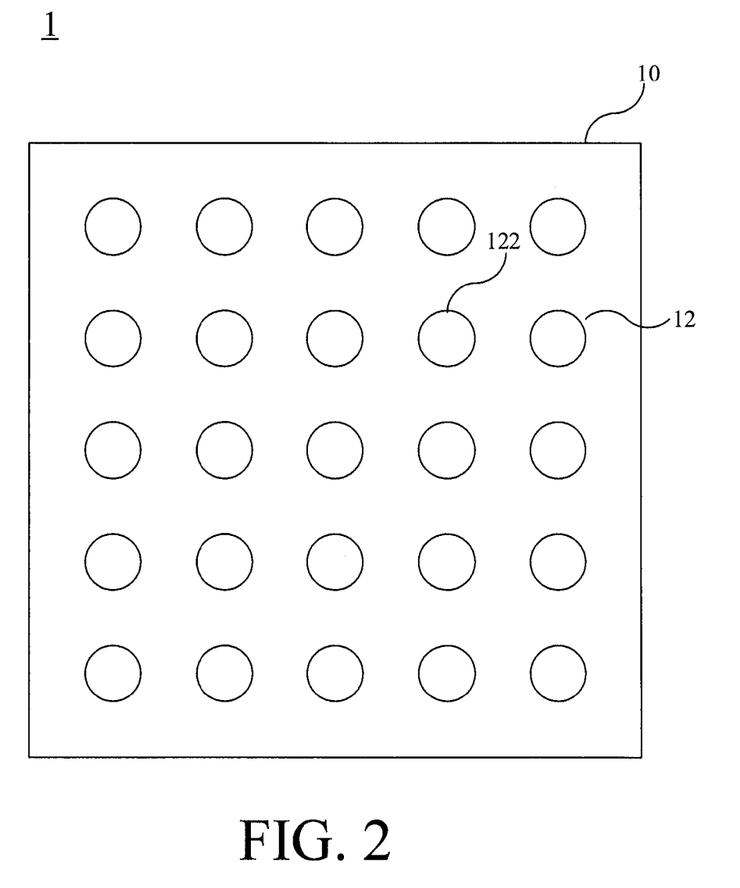
FIG. 2 shows the front view of the heavy metal detecting device of the present invention in an embodiment.

Please refer to FIG. 1 and FIG. 2. FIG. 1 shows the process flow chart of the heavy metal detecting device of the present invention in an embodiment. FIG. 2 shows the front view of the heavy metal detecting device of the present invention in an embodiment.

The present invention provides a fabricating method for the heavy metal detecting device 1, comprising the following steps of: (S1) preparing a substrate, cleaning the substrate with a first liquid, and drying the substrate with a first gas; (S2) soaking the substrate in a first solution; (S3) after soaking the substrate for a first period of time, cleaning and drying the substrate with the first liquid and the first gas respectively; (S4) soaking the substrate in a pre-synthesized nano-metal-particle solution; and (S5) after soaking the substrate for a second period of time, cleaning and drying the substrate with a second liquid and the first gas respectively. Wherein, the process of the heavy metal detecting device is done after finishing all of the steps mentioned above.

In an embodiment, the substrate of the present invention is made of the nonconductive material like polyethylene, polystyrene, polyethylene terephthalate, polycarbonate, polyetheretherketone or polytetrafluoroethene, or the conductive material like Fe, Ti, Au, Ag, Cu, Ni, Pt, Pd, Al or stainless steel.

After preparing the substrate 10, cleaning the substrate 10 with a first liquid, and drying the substrate 10 with a first gas, wherein the first liquid is ethanol and the first gas is nitrogen. After finishing the step one (S1), please getting into the step two (S2): soaking the substrate in a first solution, wherein the first solution is a silane solution, like 0.0532% 3-(trimethoxysilylprppyl)diethylenetriamine, TMS, made of 99.8% alcohol. The surface of the substrate 10 is cleaned by soaking the substrate 10 in the first solution to let the surface of the substrate exhibit the specific functional group like —$NH_2$, —COOH, —SH or —CN. After the substrate 10 is soaked in the TMS solution for the first period of time, please get into the step three (S3): cleaning and drying the substrate 10 with the first liquid and the first gas respectively. Wherein, the time period ranges from 30 minutes to 48 hours.

Please get into the step four (S4): soaking the substrate 10 in a pre-synthesized nano-metal-particle solution, wherein the solution comprises the nano-metal-particle 122. The nano-metal-particle 122 is deposited on the surface of the substrate 10 through S4 to form a nano-metal-particle array 12. In an embodiment, the nano-metal-particle 122 is, but not limited to, an Ag nano-particle (SNP). The nano-metal-particle 122 is able to be AuNP or hollow AuNP (HGN). In FIG. 2, the form of the nano-metal-particle 122 is sphere, and the form of the nano-metal-particle 122 is also able to be rod, square, line and plate, and the size of the nano-metal-particle 122 ranges from 1 nm to 200 nm.

After the substrate 10 is soaked in the nano-metal-particle solution for a second period of time, the enough amounts of the nano-metal-particles 122 are deposited on the surface of the substrate 10 and the nano-metal-particle array 12 is formed. Please get into the step 5: cleaning and drying the substrate 10 with a second liquid and the first gas respectively. Wherein, the process of the heavy metal detecting device is done after finishing all of the steps mentioned above. Wherein, the second liquid is pure water.

When detecting an analyte with the heavy mental ion, the user can shake the ion solution to make the heavy metal detecting device 1 of the present invention react with the analyte solution fast. If the solution has heavy metal ions, the nano-metal-particle 122 on the heavy metal detecting device 1 will react with the heavy metal ion and be replaced, which will make the concentration of the nano-metal-particle 122 on the heavy metal detecting device 1 decrease. After the reaction is finished, the user can observe change of the spectrum of the heavy metal detecting device 1 to identify the concentration of the heavy metal ion in the analyte.

Moreover, the heavy metal detecting device 1 which shows the consequence of the heavy metal detecting is able to be taken a picture by smart phones, cameras and any kinds of 3C products. The picture is able to be uploaded to the cloud storage by Internet for cloud calculation and collection of digital information.

Figure 3A:
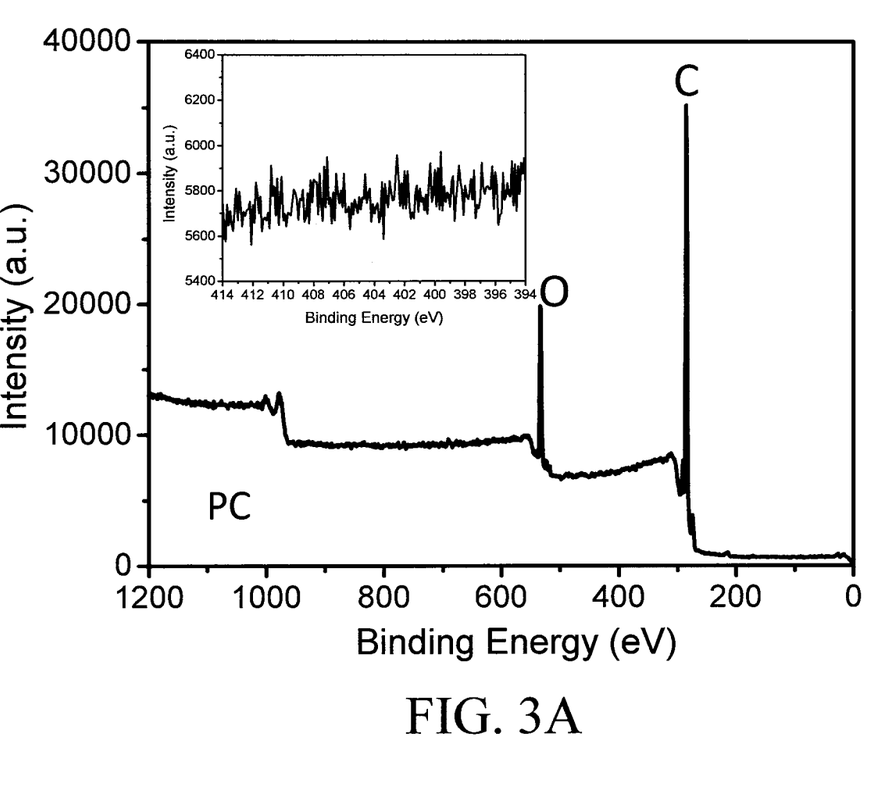
FIG. 3A shows the spectrum diagram of the x-ray photoelectron spectroscopy of the present invention in an embodiment.
Figure 3B:
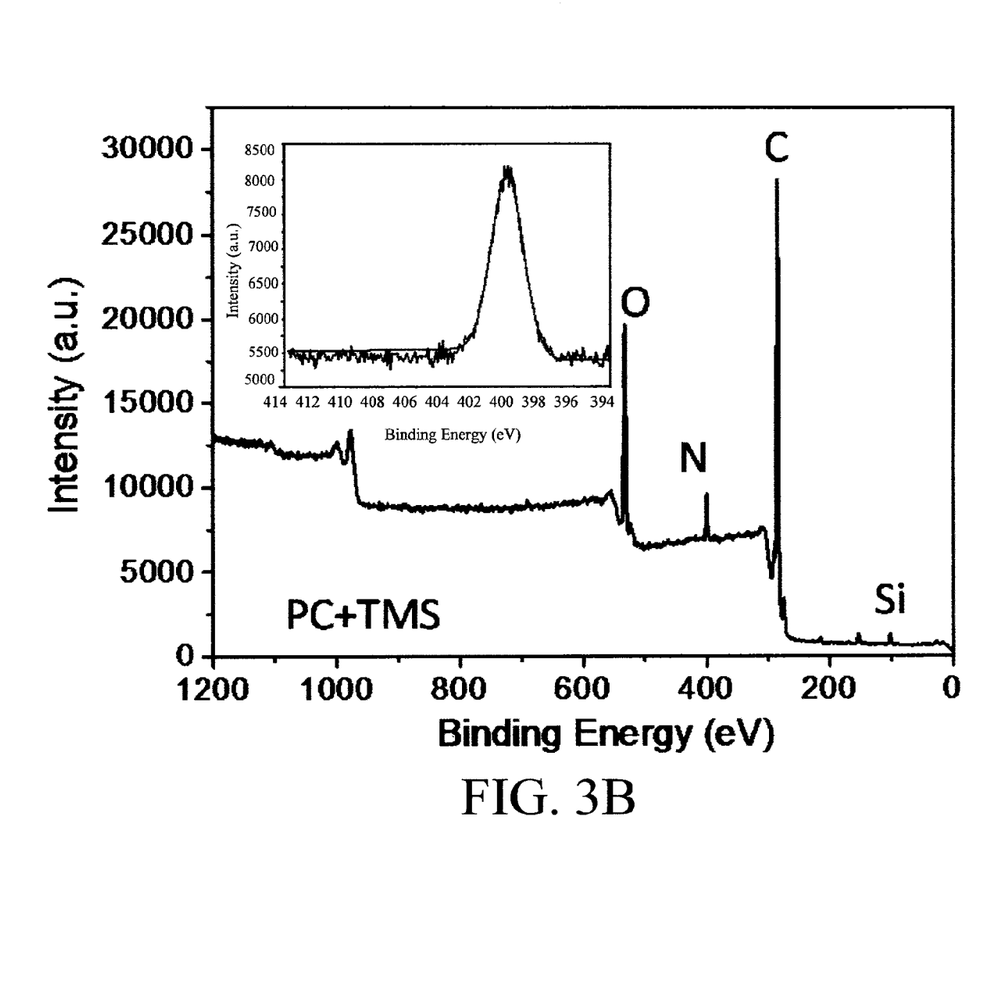
FIG. 3B shows the spectrum diagram of the x-ray photoelectron spectroscopy of the present invention in an embodiment.
Figure 3C:
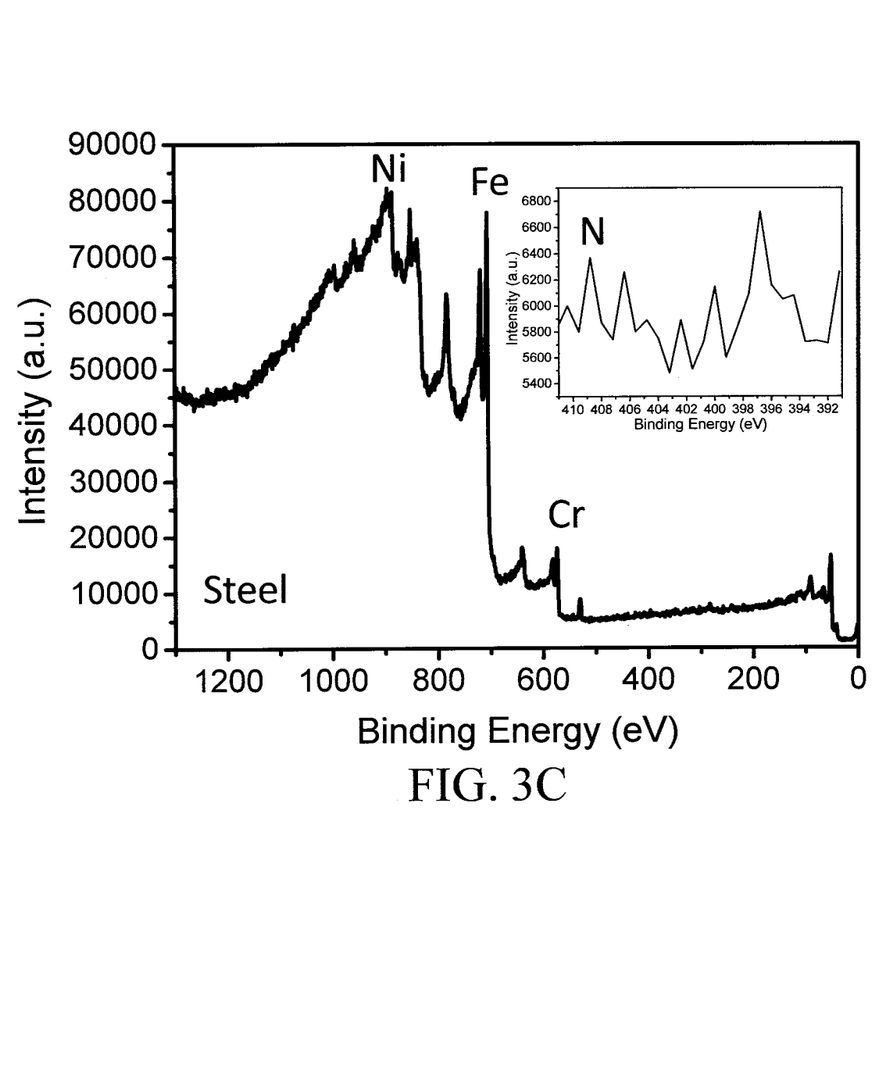
FIG. 3C shows the spectrum diagram of the x-ray photoelectron spectroscopy of the present invention in an embodiment.
Figure 3D:
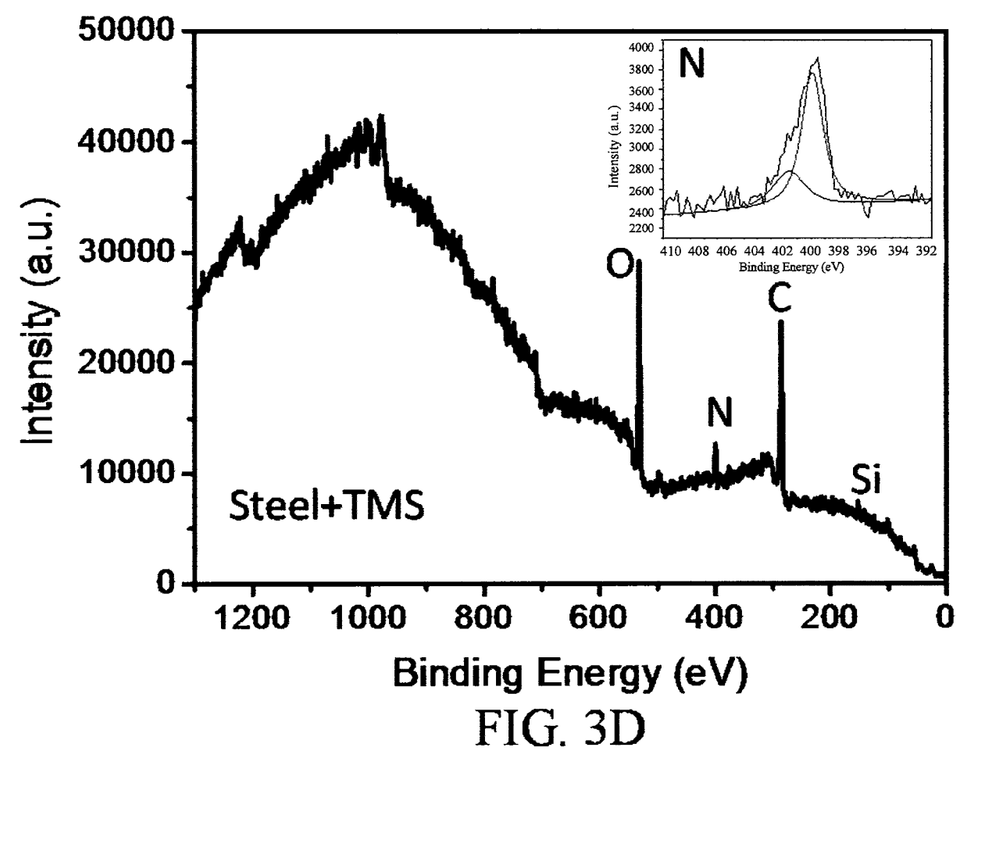
FIG. 3D shows the spectrum diagram of the x-ray photoelectron spectroscopy of the present invention in an embodiment.

Please refer to FIG. 3A, FIG. 3B, FIG. 3C and FIG. 3D, FIG. 3A, FIG. 3B, FIG. 3C and FIG. 3D show the spectrum diagram of the x-ray photoelectron spectroscopy, XPS, of the present invention in an embodiment. Wherein FIG. 3A and FIG. 3C show the x-ray photoelectron spectroscopy before the substrate is modified by TMS. The inventor wants to prove that if the different substrates are able to be modified with the siloxane exhibiting the specific functional group, especially the material whose surface has little or without —OH. The investor uses polycarbonate (PC) and stainless steel to prove it. According to the XPS, the XPS of the two kinds of the substrates is analyzed before and after TMS is modified. Because TMS has N and Si which are not comprised in the substrates (shown in FIG. 3C and FIG. 3A), it is clear in FIG. 3B and FIG. 3D that the signal of the N and Si are shown up on the PC and stainless steel after the TMS is modified. Therefore, the inventor considers that the siloxane is able to be modified even though the surface is lake of the —OH. More importantly, the substrate is cleaned by the pure water and alcohol. The substrate does not need to do extra surface process by any large devices like using plasma.

Figure 4:
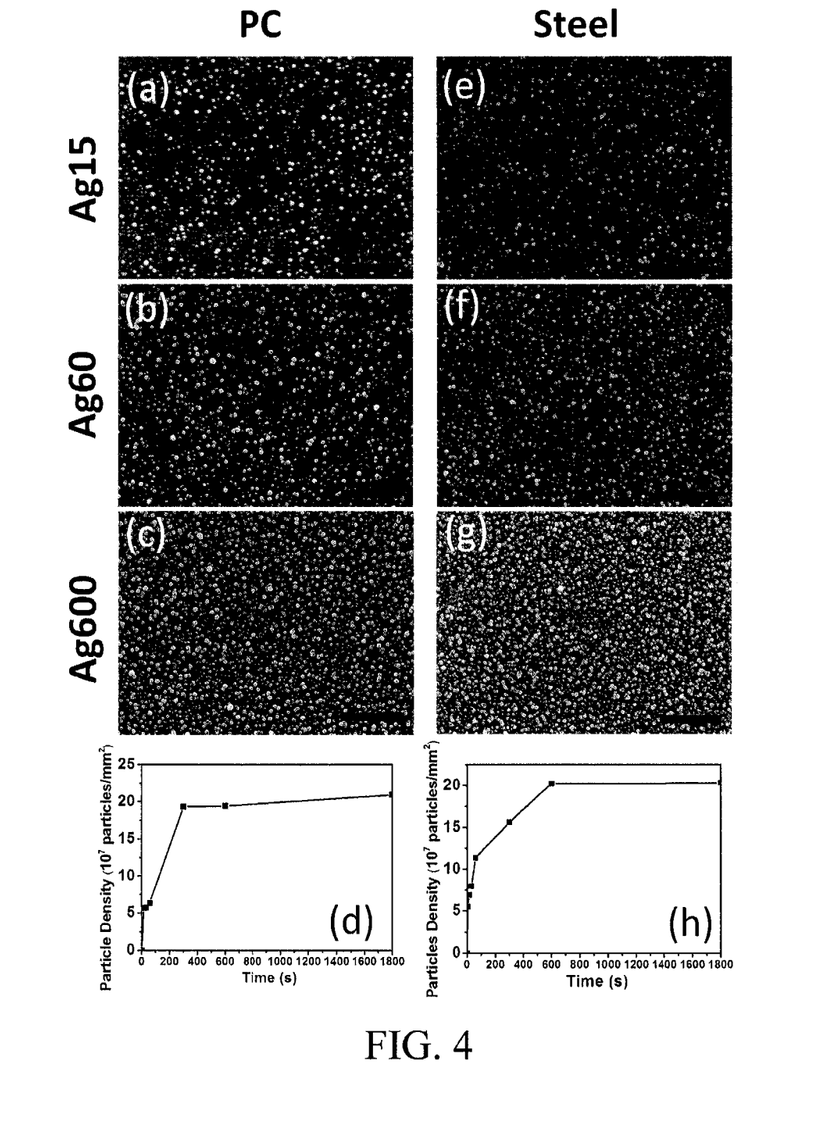

Please refer to FIG. 4. FIG. 4 shows the photography from the scanning electron microscope of the present invention in an embodiment. The inventor observes the surface of PC substrate and stainless steel substrate with the nano-metal-particle array. The present invention uses Ag nano-particle to be the nano-metal-particle. The density of the nano-metal-particle is controlled by changing the time period of soaking into the nano-metal-particle solution like 15 seconds (Ag15), 60 seconds (Ag60) and 600 seconds (Ag600). According to the photography from the scanning electron microscope, it is shown that the density of the particles increases on the two kinds of the substrates as time goes on.

According to FIG. 4(d) and FIG. 4(f), the density of the particles increases when time is passing. And the maximum density is shown up after three minutes and ten minutes when the substrates are made of PC and stainless steel respectively. According to the micro-photograph, Ag nano-array with single-layer, high-density, even distribution is disposed on the polymer and metal substrates; more importantly, the density of the nano-particles is adjustable. The nano-metal-particle array is a single-layer structure without stacking on every substrate, which makes every nano-particle reacts with the heavy metal ion in solution fully.

Figure 5:
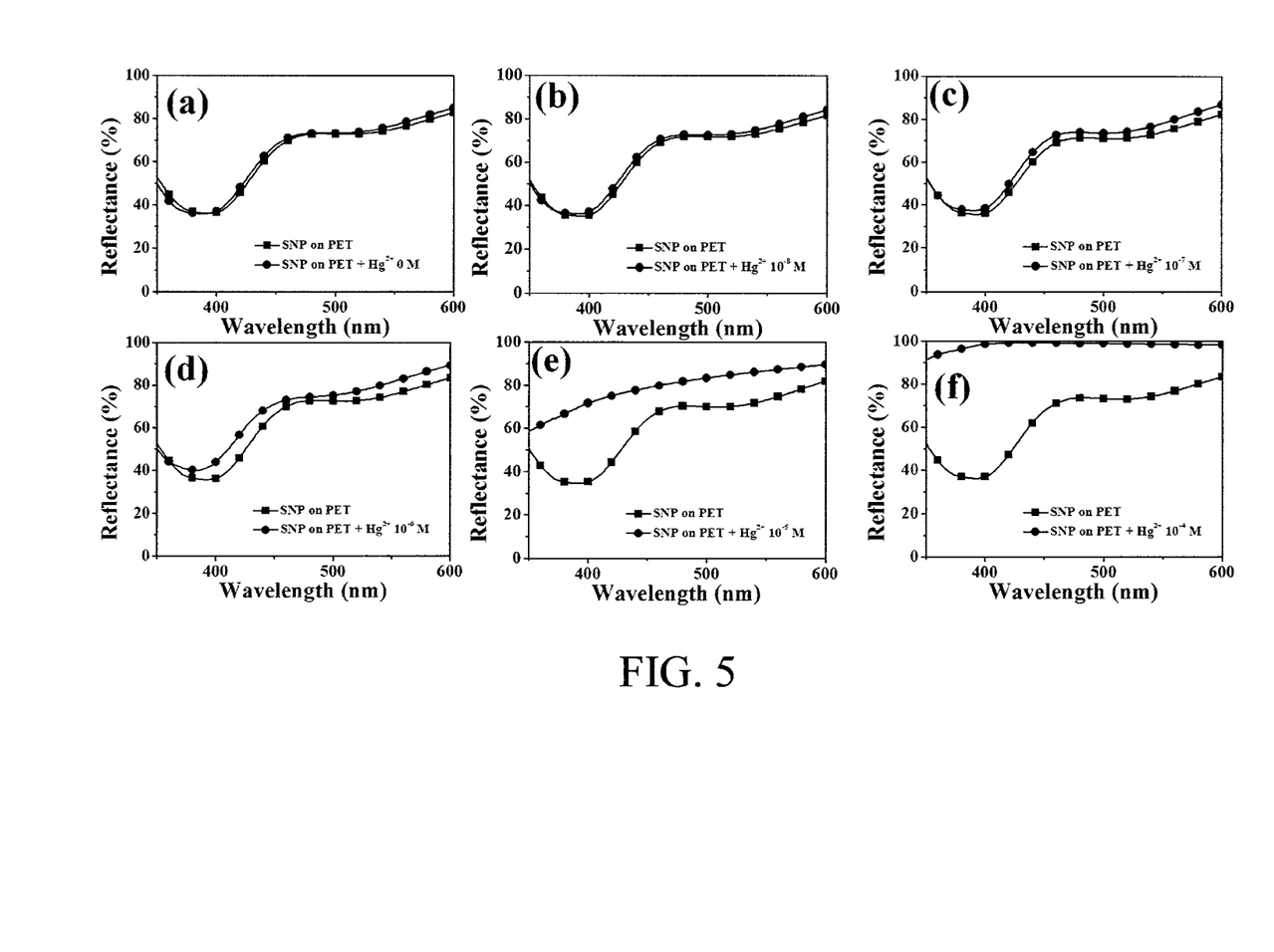

The inventor analyzes the reflectance spectrum of the heavy metal detecting device 1 to discuss the consequence after the heavy metal detecting device 1 reacts with the heavy metal ion solution with different concentration. Please refer to FIG. 5; FIG. 5 shows the spectrum diagram of the reflective light of the heavy metal detecting device before and after reacting with the heavy metal ions with the different concentration. Wherein FIG. 5(a) to FIG. 5(f) are the reflectance spectra of the heavy metal detecting device before and after reacting with Hg ion which is (a) 0 M, (b) $10^{-8}$ M, (c) $10^{-7}$ M, (d) $10^{-6}$ M, (e) $10^{-5}$ M and (f) $10^{-4}$ M respectively.

In the embodiment, the Hg ion is a heavy metal ion, the white PET is a substrate of the detecting device, and the Ag nano-particles (SNPs) are disposed on the heavy metal detecting device. Firstly, there is an obvious valley at 396 nm on the reflectance spectrum of the detecting device without reacting because SPR of the Ag nano-particle decreases the reflection of the PET. In FIG. 5(a), the change of the spectrum of the detecting device made of PET before and after reacting with pure water is not obvious. That is to say, the waterproof characteristic makes the optical property of PET not be affected by the water. When the concentration of Hg ion is higher, the consumption of Ag nano-particles gets higher and the reflectance is raised up obviously. More importantly, when the concentration of Hg ion is $10^{-8}$ M, the line in the spectrum of the reflectance lightly rises up at SPR, shown in FIG. 5(b).

Figure 6:
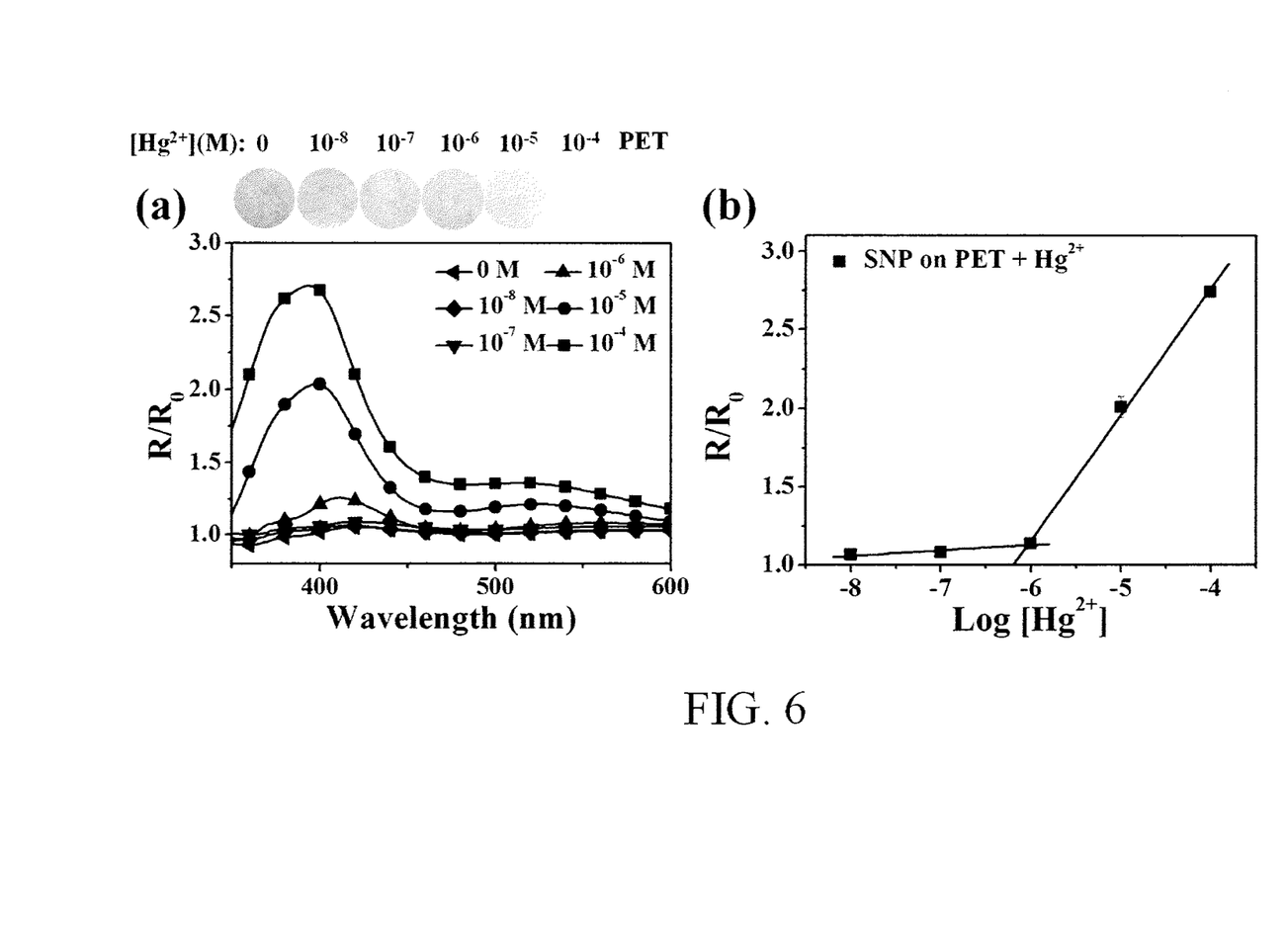
FIG. 6 shows (a) the spectrum of the reflectance ratio of the heavy metal detecting device before and after being reacted with the Hg ions with different concentration (b) the relationship between the reflectance ratio at the specific wavelength and the Hg ions concentration.

Please refer to FIG. 6; FIG. 6 shows (a) the spectrum of the reflectance ratio of the heavy metal detecting device before and after being reacted with the Hg ions with different concentration and (b) the relationship between the reflectance ratio at the specific wavelength and Hg ions concentration. The investor analyzes the change of the reflectance ratio before and after the heavy metal device reacts with the Hg ions. According to FIG. 6, the concentration of Hg ions increases and the reflectance ratio at the SPR increases as well. Besides, according to the photograph, the color of the Ag nano-particles disappears gradually when the Hg ion concentration increases. Despite the concentration of the Hg ions is only $10^{-8}$ M, the change of the color is detectable by eyes. Besides, the change of the reflectance ratio at the specific wavelength shows the two linear relationships with the concentration of the Hg ions. The change of the spectrum is obvious when the concentration ranges from $10^{-6}$ M to $10^{-4}$ M and from $10^{-8}$ M to $10^{-6}$ M. Wherein, the lowest detectable concentration of the heavy metal detecting device 1 is $10^{-8}$ M, 0.002 mg/L.

From the above mention, the present invention provides a fabricating method for the heavy metal detecting device, comprising the following steps: preparing a substrate, cleaning the substrate with a first liquid, and drying the substrate with a first gas; soaking the substrate in a first solution; after soaking the substrate for a first period of time, cleaning and drying the substrate with the first liquid and the first gas respectively; soaking the substrate in a pre-synthesized nano-metal-particle solution; and after soaking the substrate for a second period of time, cleaning and drying the substrate with a second liquid and the first gas respectively. Wherein, a process of the heavy metal detecting device is done after finishing all of the steps mentioned above. Moreover, the present invention provides a heavy metal detecting device made by processing the steps mentioned above. The heavy metal detecting device is used to detect the concentration of heavy metal ions. The heavy metal detecting device comprises a substrate and a nano-metal-particle array, wherein the nano-metal-particle array comprises nano-metal-particles.

Comparing with the familiar art, the present invention provides a heavy metal detecting device having the advantages of simplicity and rapidity in the detecting method. Moreover, the heavy metal detecting device is light, equipped with high sensitivity for detecting the concentration of the heavy metal ion in the analyte. The present invention provides a heavy metal detecting device to form a layer of the nano-metal-particle on the surface of the nonconductive substrate to process the fabricating of the heavy metal detecting device. The heavy metal detecting device is a portable and rapid detection platform with low-cost, stability and high sensitivity.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A fabricating method for a heavy metal detecting device, comprising the following steps of:
   (S1) cleaning a nonconductive substrate with ethanol, and drying the nonconductive substrate with nitrogen;
   (S2) soaking the nonconductive substrate in a liquid with silane molecules;
   (S3) after soaking the nonconductive substrate for a first period of time, cleaning and drying the substrate with the ethanol and the nitrogen respectively;
   (S4) soaking the nonconductive substrate in a pre-synthesized nano-metal-particle solution for a second period of time; and
   (S5) cleaning and drying the nonconductive substrate with pure water and the nitrogen respectively;
   wherein the first period of time is in a range from 30 minutes to 48 hours, and the second period of time is less than or equal to 10 minutes.

2. The fabricating method for the heavy metal detecting device of claim 1, wherein the nonconductive substrate is able to be replaced by a conductive substrate, and a material of the conductive substrate is one in a group of: Fe, Ti, Au, Ag, Cu, Ni, Pt, Pd, Al or stainless steel.

3. The fabricating method for the heavy metal detecting device of claim 1, wherein a material of the nonconductive substrate is one in a group of: polyethylene, polystyrene, polyethylene terephthalate, polycarbonate, polyetheretherketone or polytetrafluoroethene.

4. The fabricating method for the heavy metal detecting device of claim 1, wherein the nano-metal-particle is Ag nanoparticle (SNP), Au nanoparticle (AuNP) or hollow Au nanoparticle (HGN), a form of the nano-metal-particle is sphere, rod, square, line, or plate.

* * * * *